(12) United States Patent
Shimaoka et al.

(10) Patent No.: US 12,618,834 B2
(45) Date of Patent: May 5, 2026

(54) MEASUREMENT SAMPLE PREPARATION METHOD, ANALYSIS METHOD, REAGENT, AND REAGENT KIT

(71) Applicants: SYSMEX CORPORATION, Kobe (JP); OSAKA UNIVERSITY, Suita (JP); NATIONAL INSTITUTE OF ADVANCED INDUSTRIAL SCIENCE AND TECHNOLOGY, Tokyo (JP)

(72) Inventors: Yuki Shimaoka, Kobe (JP); Masaya Okada, Kobe (JP); Shigeki Iwanaga, Kobe (JP); Kazuki Bando, Suita (JP); Katsumasa Fujita, Suita (JP); Yasunori Nawa, Ikeda (JP); Satoshi Fujita, Ikeda (JP)

(73) Assignees: SYSMEX CORPORATION, Kobe (JP); OSAKA UNIVERSITY, Osaka (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 995 days.

(21) Appl. No.: 17/686,784

(22) Filed: Mar. 4, 2022

(65) Prior Publication Data

US 2022/0283154 A1     Sep. 8, 2022

(30) Foreign Application Priority Data

Mar. 5, 2021   (JP) ................................ 2021-035593
Mar. 5, 2021   (JP) ................................ 2021-035597

(51) Int. Cl.
G01N 33/543 (2006.01)
G01N 21/25 (2006.01)
(Continued)

(52) U.S. Cl.
CPC ..... G01N 33/54353 (2013.01); G01N 21/255 (2013.01); G01N 21/314 (2013.01);
(Continued)

(58) Field of Classification Search
CPC ........... G01N 33/54353; G01N 21/255; G01N 21/314; G01N 21/658; G01N 33/54346;
(Continued)

(56) References Cited

U.S. PATENT DOCUMENTS 6,348,318 B1 * 2/2002 Valkirs ............... C07K 16/1282
435/7.1
10,801,964 B2 10/2020 Lednev
(Continued)

FOREIGN PATENT DOCUMENTS

CN        111033230 A     4/2020
JP         4-163600 A      6/1992
(Continued)

OTHER PUBLICATIONS

Filbrun, Seth L., et al. "Chemical modification of antibodies enables the formation of stable antibody—gold nanoparticle conjugates for biosensing." Analyst 142.23 (2017): 4456-4467. (Year: 2017).*
(Continued)

*Primary Examiner* — Bao-Thuy L Nguyen
*Assistant Examiner* — Christopher Evans
(74) *Attorney, Agent, or Firm* — Sughrue Mion, PLLC

(57)                    ABSTRACT

Disclosed is a preparation method for preparing a measurement sample comprising an aggregate of metal nanoparticles having an analyte bound thereto, the preparation method comprising: contacting the analyte with a linker to bind the analyte to the linker; and contacting the linker that has been bound to the analyte with the metal nanoparticles to bind the linker to the metal nanoparticles.

9 Claims, 12 Drawing Sheets

(51) Int. Cl.

| | | |
|---|---|---|
| *G01N 21/31* | (2006.01) | |
| *G01N 21/65* | (2006.01) | |
| *G01N 33/58* | (2006.01) | |
| *G01N 33/68* | (2006.01) | |
| *G06N 3/08* | (2023.01) | |
| *G16C 20/20* | (2019.01) | |
| *G16C 20/70* | (2019.01) | |

(52) U.S. Cl.
CPC ..... *G01N 21/658* (2013.01); *G01N 33/54346* (2013.01); *G01N 33/588* (2013.01); *G01N 33/6812* (2013.01); *G06N 3/08* (2013.01); *G16C 20/20* (2019.02); *G01N 2201/121* (2013.01); *G01N 2201/1296* (2013.01); *G16C 20/70* (2019.02)

(58) Field of Classification Search
CPC . G01N 33/588; G01N 2201/121; G16C 20/20
USPC .......................................... 435/975; 436/518
See application file for complete search history.

(56)                     References Cited

U.S. PATENT DOCUMENTS

| | | | |
|---|---|---|---|
| 11,379,709 | B2 | 7/2022 | Troy et al. |
| 11,428,638 | B2 | 8/2022 | Xie et al. |
| 2007/0155021 | A1 | 7/2007 | Zhang et al. |
| 2010/0035243 | A1 | 2/2010 | Muller et al. |
| 2015/0177152 | A1 | 6/2015 | Thomas et al. |
| 2019/0250105 | A1 | 8/2019 | Mahadevan-Jansen et al. |
| 2020/0003678 | A1 | 1/2020 | Wolf et al. |
| 2020/0284657 | A1 | 9/2020 | Leblond et al. |
| 2020/0300768 | A1 | 9/2020 | Hikita et al. |
| 2020/0408789 | A1 | 12/2020 | Kawamura et al. |
| 2021/0055211 | A1 | 2/2021 | Nagamori et al. |
| 2021/0156784 | A1 | 5/2021 | Hanashi |
| 2021/0247233 | A1 | 8/2021 | Aizawa et al. |
| 2021/0248417 | A1 | 8/2021 | Taya et al. |
| 2022/0101276 | A1 | 3/2022 | Banatao et al. |
| 2022/0390351 | A1 | 12/2022 | Saleh et al. |

FOREIGN PATENT DOCUMENTS

| | | |
|---|---|---|
| JP | 2007-192552 A | 8/2007 |
| JP | 2007-534291 A | 11/2007 |
| JP | 2008-267952 A | 11/2008 |
| JP | 2020-71166 A | 5/2020 |
| JP | 2020-101524 A | 7/2020 |
| JP | 6778451 B1 | 11/2020 |
| WO | 2007/044025 A2 | 4/2007 |
| WO | 2016/139479 A1 | 9/2016 |
| WO | 2019/073666 A1 | 4/2019 |
| WO | 2019/077955 A1 | 4/2019 |
| WO | 2020/196074 A1 | 10/2020 |

OTHER PUBLICATIONS

Penn, Michelle A., David M. Drake, and Jeremy D. Driskell. "Accelerated surface-enhanced Raman spectroscopy (SERS)-based immunoassay on a gold-plated membrane." Analytical Chemistry 85.18 (2013): 8609-8617. (Year: 2013).*

Taiwei Lu et al., "Spectroscopy and Hybrid Neural Network Analysis", Proceedings of the IEEE, vol. 84, No. 6, Jun. 1996, pp. 895-905 (11 pages).

Non-final Office Action dated Mar. 7, 2023, issued in U.S. Appl. No. 17/686,802.

Acquarelli et al., "Convolutional neural networks for vibrational spectroscopic data analysis", Analytica Chimica Acta, 2017, vol. 954, pp. 22-31 (10 pages total).

Liu et al., "Deep Convolutional Neural Networks for Raman Spec-trum Recognition: A Unified Solution", Analyst, Nov. 7, 2017, vol. 21, pp. 1-8 (8 pages total).

Fukuhara et al., "Feature visualization of Raman spectrum analysis with deep convolutional neural network", Analytica Chimica Acta, 2019, vol. 1087, pp. 11-19 (9 pages total).

Dojindo Laboratories, Catalog of "Protein cross-linkers and label-ing agents", Aug. 28, 2019, pp. 144-188, https://www.dojindo.co.jp/technical/catalog/08.pdf (49 pages total).

Weng et al., "Deep learning networks for the recognition and quantitation of surface-enhanced Raman spectroscopy", Analyst, 2020, vol. 145, pp. 4827-4835 (9 pages total).

Portela et al., "Highly sensitive SERS analysis of the cyclic Arg—Gly—Asp peptide ligands of cells using nanogap antennas", Journal of Biophotonics, 2017, vol. 10, No. 2, pp. 294-302 (9 pages total).

Huang et al., "SERS discrimination of single amino acid residue in single peptide by plasmonic nanocavities", Arxiv.org, Aug. 9, 2019, (22 pages total).

Extended European Search Report issued Jul. 27, 2022 in European Application No. 22160175.0.

Extended European Search Report issued Jul. 20, 2022 in European Application No. 22160173.5.

Office Action issued on Dec. 21, 2023 by the United States Patent and Trademark Office in U.S. Appl. No. 17/686,802.

Communication Issued Jun. 4, 2024 in European Application No. 22 160 173.5.

Final Office Action dated Aug. 9, 2023 in U.S. Appl. No. 17/686,802.

Communication dated Jan. 22, 2025 in Japanese Application No. 2021-035597.

Communication dated Sep. 26, 2025, from the European Patent Office in European Application No. 22 160 175.0.

Communication issued Jun. 18, 2025 in Japanese Application No. 2021-035597.

* cited by examiner

EXAMPLES

COMPARATIVE EXAMPLES

MEASUREMENT SAMPLE PREPARATION METHOD, ANALYSIS METHOD, REAGENT, AND REAGENT KIT

CROSS REFERENCE TO RELATED APPLICATIONS

This application claims priority from prior Japanese Patent Application No. 2021-035597, filed on Mar. 5, 2021, entitled "MEASUREMENT SAMPLE PREPARATION METHOD, ANALYSIS METHOD, REAGENT, AND REAGENT KIT", and prior Japanese Patent Application No. 2021-035593, filed on Mar. 5, 2021, entitled "METHOD FOR ANALYZING TEST SUBSTANCE, ANALYZER, TRAINING METHOD, ANALYZER SYSTEM, AND ANALYSIS PROGRAM", the entire contents of which are incorporated herein by reference.

FIELD OF THE INVENTION

The present invention relates to: a preparation method for preparing a measurement sample containing an aggregate of metal nanoparticles having an analyte bound thereto; an analysis method; a reagent; and a reagent kit.

BACKGROUND

US Patent Application Publication No. 2007/0155021 discloses a surface enhanced Raman scattering (SERS) active particle which comprises a metal-containing particle and a cationic coating provided on the metal-containing particle and carries a positive electric charge. US Patent Application Publication No. 2007/0155021 also discloses a SERS active particle which includes a metal-containing particle and a non-metal molecule, in which the metal-containing particle is derivatized with the non-metal molecule. US Patent Application Publication No. 2007/0155021 also discloses a method in which an analyte is contacted with SERS active particles to capture the analyte on the SERS active particles, the SERS active particles each having the analyte captured thereon are agglutinated, and a signal of a SERS spectrum is detected.

The highly sensitive detection of an analyte has been required in various fields. For example, in a clinical test, it has been required to detect an amino acid in a protein with high sensitivity. In US Patent Application Publication No. 2007/0155021, detection sensitivity is improved by enhancing a signal of a SERS spectrum using a SERS active particle. However, further enhancement of the signal is still required.

An object of the present invention is to provide: a measurement sample preparation method whereby the sensitivity of detection of an analyte can be improved; an analysis method; a reagent for preparing a measurement sample; and a reagent kit.

SUMMARY OF THE INVENTION

The scope of the present invention is defined solely by the appended claims, and is not affected to any degree by the statements within this summary.

The present invention relates to a preparation method for preparing a measurement sample including an aggregate of metal nanoparticles bound to an analyte, the preparation method including: contacting the analyte with a linker to bind the analyte to the linker; and contacting the linker that has been bound to the analyte with the metal nanoparticles to bind the linker to the metal nanoparticles. It becomes possible to prepare a measurement sample whereby an analyte contained therein can be detected with high sensitivity.

The present invention relates to an analysis method including: obtaining an optical spectrum from the measurement sample prepared by the preparation method; and outputting information about the analyte on the basis of the obtained optical spectrum. It becomes possible to detect the analyte with high sensitivity.

The present invention relates to a reagent for use in the preparation of a measurement sample by the above-mentioned preparation method, the reagent including a linker that is not bound to a metal nanoparticle.

The present invention relates to a reagent kit for use in the preparation of a measurement sample by the above-mentioned preparation method, the reagent kit including: the reagent; and metal nanoparticles that are packed separately from a linker.

According to the present invention, the sensitivity of detection of an analyte can be improved.

BRIEF DESCRIPTION OF THE DRAWINGS

In FIG. 4, the symbol "a" indicates a spectrum obtained when an analyte is added, and the symbol "b" indicates a spectrum of a negative control which is obtained when the analyte is not added;

In FIG. 5, the symbol "c" indicates a spectrum of a negative control which is obtained when the analyte is not added;

In FIG. 9, the symbol "a" indicates a spectrum of the measurement sample composed of only gold nanoparticles, and the symbol "b" indicates a spectrum of the measurement sample prepared by mixing only gold nanoparticles and DSP with each other;

DETAILED DESCRIPTION OF THE PREFERRED EMBODIMENTS

1. Measurement Sample Preparation Method

Figure 1:
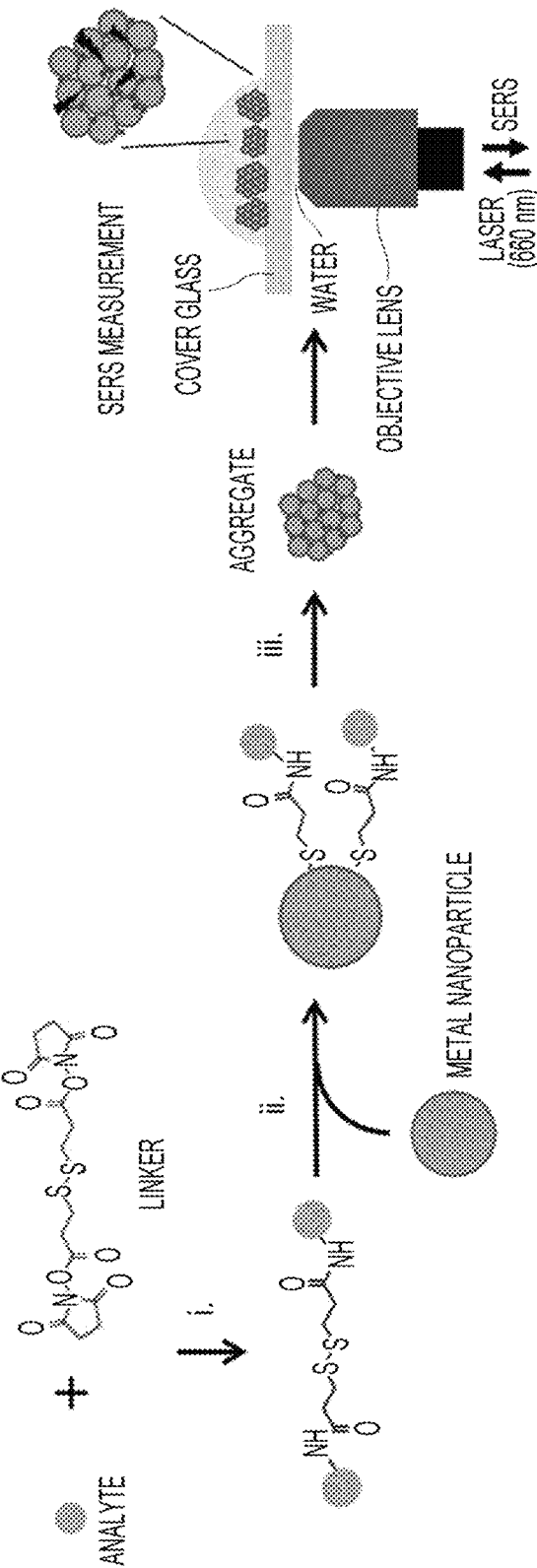
FIG. 1 is a diagram showing a measurement sample preparation method.

According to the preparation method, it becomes possible to prepare a measurement sample including an aggregate of metal nanoparticles bonded to an analyte. As shown in FIG. 1, the preparation method includes (i) contacting the analyte with the linker to bind the analyte to the linker and (ii) contacting the linker that has been bound to the analyte with the metal nanoparticles to bind the linker to the metal nanoparticles. The method may further include (iii) adding an inorganic salt or an acid, subsequent to the contact of the linker that has been bound to the analyte with the metal nanoparticles, depending on the type of the analyte.

In the preparation method, the analyte and the linker are reacted with each other in advance, and subsequently a complex of the analyte and the liker is reacted with the metal nanoparticles. As a result, the sensitivity of the detection of the analyte can be improved.

The measurement sample is preferably a sample which can be subjected to a spectroscopic analysis of the analyte. Examples of the spectroscopic analysis include fluorescence spectroscopy, surface plasmon resonance (SPR) and infrared spectroscopy. The spectroscopic analysis is preferably Raman scattering spectroscopy, more preferably surface enhanced Raman scattering (SERS) spectroscopy.

(i) Contact of Analyte with Linker

The analyte can include at least one component selected from the group consisting of a nucleic acid (e.g., RNA, DNA), an amino acid, a polypeptide, a catecholamine, a polyamine, an organic acid, an extracellular vesicle and a virus. The term "polypeptide" as used herein refers to a compound having a structure that two or more amino acid residues are linked to each other through a peptide bond. Examples of the polypeptide include a dipeptide, an oligopeptide and a protein.

The analyte has at least one functional group selected from an amino group, a carboxyl group and a hydroxyl group. The analyte binds to the below-mentioned linker by utilizing the functional group.

The analyte is contained in a solvent such as water and a buffer solution. Alternatively, the analyte is contained in a liquid biological sample such as blood, serum, plasma, saliva, ascitic fluid, pleural effusion, cerebrospinal fluid, interstitial fluid and urine.

The linker has a reactive group capable of reacting with the functional group. The linker is not particularly limited, as long as the linker can bind to the below-mentioned metal nanoparticles. For example, the linker is represented by general formula (I).

$$R^3—O—CO—R^1—S—S—R^2—CO—O—R^4 \qquad (I)$$

(In the formula, $R^1$ and $R^2$ may be the same as or different from each other, and independently represent an alkylene group having 1 to 12 carbon atoms; and $R^3$ and $R^4$ may be the same as or different from each other, and independently represent a reactive group.)

It is preferred that the number of carbon atoms constituting each of $R^1$ and $R^2$ is 2 to 10. It is more preferred that $R^1$ and $R^2$ are the same as each other.

Each of $R^3$ and $R^4$ represents a reactive group capable of reacting with the functional group in the analyte. It is preferred that $R^3$ and $R^4$ are the same as each other. When the functional group in the analyte is an amino group, examples of the reactive group include an N-hydroxysuccinimide ester group, an isothiocyanate group, an isocyanate group, an acyl azide group, a sulfonyl chloride group, an aldehyde group, an imide ester group, a fluorobenzene group, an epoxide group, a carbodiimide group, a carbonate group, and a fluorophenyl ester group. It is preferred that the reactive group is an N-hydroxysuccinimide ester group.

When the reactive group is an N-hydroxysuccinimide ester group, the linker preferably includes at least one component selected from the group consisting of dithiobis (succinimidyl propionate), dithiobis(succinimidyl undecanoate), dithiobis(succinimidyl octanoate) and dithiobis (succinimidyl hexanoate).

When the functional group in the analyte is a carboxyl group, examples of the reactive group include a hydroxyl group and an amino group.

When the functional group in the analyte is a hydroxyl group, examples of the reactive group include an N-hydroxysuccinimide ester group, an isothiocyanate group, an isocyanate group, an acyl azide group, a sulfonyl chloride group, an aldehyde group, an imide ester group, a fluorobenzene group, an epoxide group, a carbodiimide group, a carbonate group, and a fluorophenyl ester group.

A single type of linker may be used, or a mixture of two or more types of linkers may be used.

In the sample containing the analyte, it is preferred to contain the analyte in an amount of, for example, about 1 nM to about 1 mM. However, in a sample containing an analyte, the content of the analyte may be unknown. In this case, the requirement of the above-mentioned analyte content is not necessarily applied. It is preferred that the pH value of the sample containing the analyte is, for example, about 6 to about 8. Therefore, when the analyte is not a liquid sample, it is preferred to dissolve the analyte in a buffer solution having a pH value of about 6 to about 8, such as PBS.

It is preferred that the linker is dissolved in an organic solvent, such as dimethyl sulfoamide and dimethyl sulfoxide, at a concentration of about 1 nM to about 1 mM.

About 1 μL to about 1 mL of a sample containing an analyte is mixed with about 1 μL to about 1 mL of a linker solution, and the resultant mixture is left to stand or is stirred at about 18° C. to about 28° C. for about 0.5 hour to about 5 hours, preferably about 1 hour to about 3 hours. In this manner, the analyte can contact with the linker to bind the analyte to the linker.

It is preferred that the pH value of the reaction solution in which the analyte is to be contacted with the linker is about 6 to about 8. This pH value is close to that in a biological environment. Therefore, a liquid sample collected from a living body can be used without any modification in the preparation of a measurement sample.

(ii) Contact of Linker Having Analyte Bound Thereto with Metal Nanoparticles

As the metal nanoparticles, nanoparticles of at least one metal selected from the group consisting of gold, silver, platinum, copper and palladium can be used. The particle diameter of each of the metal nanoparticles is, for example, equal or greater than 10 nm and equal or smaller than 150 nm. The particle diameter is preferably 40 nm to 80 nm, more preferably 40 nm or 80 nm. The shape of each of the metal nanoparticles is not limited. Metal nanoparticles each having a spherical, rod-like, shell-like, cube-like, triangular plate-like, star-like or wire-like shape can be used. Preferably used are spherical metal nanoparticles. The metal nanoparticles are commercially available from, for example, BBI Solutions or the like, and the commercially available products can be used. The method for measuring the particle diameter or the particle shape is performed in accordance with the instructions provided by a manufacturer. The particle diameter is a volume-based median diameter which is measured using a particle size distribution measurement device by a laser diffraction/scattering method. As the particle size distribution measurement device, "Microtrac MT3000II" manufactured by Nikkiso Co., Ltd. and the like can be used. The term "particle diameter" as used herein refers to a diameter.

The contact between the linker having the analyte bound thereto and the metal nanoparticles is not particularly limited, as long as the contact is performed under the conditions where the linker can be bound to the surface of each of the metal nanoparticles.

For example, about 1 μL to about 1 mL of the reaction solution that has been prepared in (i) by contacting the analyte with the linker is diluted with the same volume of water (preferably ultrapure water), and then about 10 μL to about 1 mL of a metal nanoparticle solution (about $9.0 \times 10^5$ to $9.0 \times 10^{15}$ particles/mL) is added to the diluted solution. This mixed solution is left to stand or is stirred at about 18° C. to about 28° C. for about 5 minutes to about 120 minutes, preferably about 10 minutes to about 60 minutes. In this manner, the linker that has been bound to the analyte is contacted with the metal nanoparticles. As a result, an aggregate of the linker that has been bound to the analyte and the metal nanoparticles can be formed. It is preferred to perform the mixing of the linker that has been bound to the analyte with the metal nanoparticles on a glass-bottomed plate.

As a substance for promoting the formation of the aggregate, an inorganic salt or an acid may be added to the reaction system. An example of the inorganic salt is sodium chloride. An example of the acid is trifluoroacetic acid. The concentration of the inorganic salt is not particularly limited, as long as the effect to promote the formation of the aggregate can be exerted. For example, the final concentration of the inorganic salt may be 10 mM to 100 mM. The concentration of the acid is not particularly limited, as long as the effect to promote the formation of the aggregate can be exerted. For example, the final concentration of the acid may be 10 mM to 100 mM. After the mixing of the inorganic salt or the acid, the reaction system is left to stand or is stirred at 4° C. to 30° C. for 1 hour to 24 hours. In this manner, an aggregate of the metal nanoparticles can be formed.

2. Analysis Method

Hereinafter, an analysis device for analyzing a measurement sample prepared by the preparation method mentioned in 1, and an analysis method which the analysis device performs are described.

Figure 2:
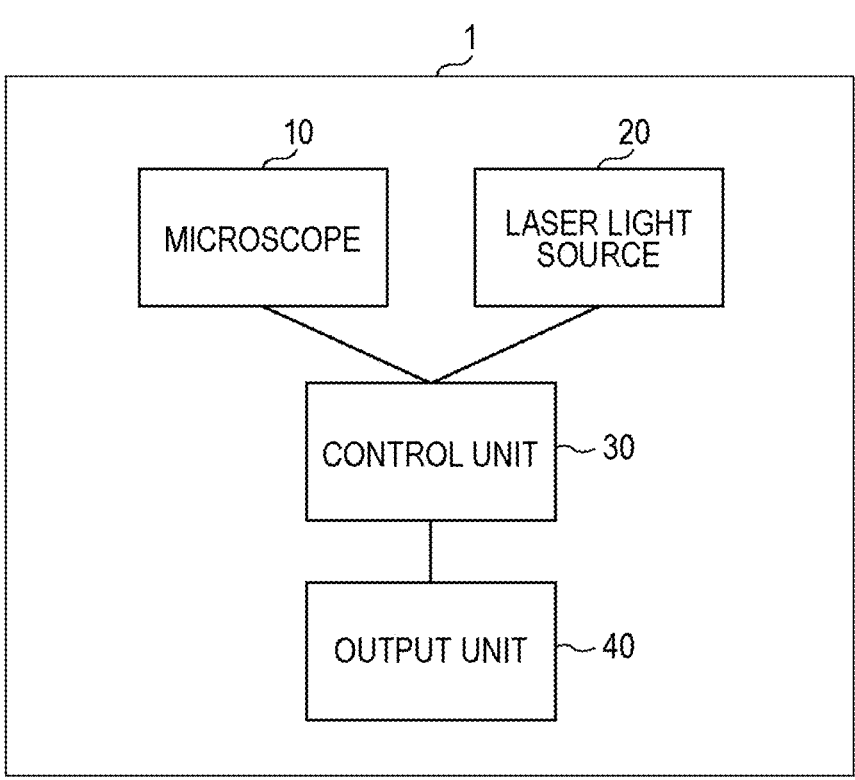
FIG. 2 is a diagram showing an example of the configuration of an analysis device.

A schematic illustration of the configuration of the analysis device 1 is shown in FIG. 2. The analysis device 1 is provided with: a microscope 10 for observing aggregates; a laser light source 20 for supplying excitation light that is emitted to a measurement sample by the microscope 10; a control unit 30 for controlling the microscope 10 and the laser light source 20; and an output unit 40 connected to the control unit 30. Examples of a device equipped with the microscope 10 and the laser light source 20 include a slit-scanning confocal Raman microscope and a multi-focus Raman microscope. The control unit 30 may be a general-purpose computer.

The control unit 30 controls in such a manner that the laser light source 20 can emit excitation light, and the control unit 30 obtains an image from the microscope 10.

When the microscope 10 is a slit-scanning confocal Raman microscope, the control unit 30 performs analysis under, for example, the following conditions.

Excitation wavelength: 660 nm
Excitation intensity: 2.5 mW/μm$^2$
Exposure time: 0.5 sec/line
Objective lens: ×40 NA1.25

These conditions may be adjusted appropriately depending on the type of the analyte, the material for the metal nanoparticles, and the shape of the metal nanoparticles.

Under these conditions, the laser irradiation is performed in a line irradiation mode. However, the laser irradiation may be performed in a spot irradiation mode.

The control unit 30 obtains an optical spectrum from the measurement sample, and the control unit 30 outputs information about the analyte to the output unit 40 on the basis of the obtained optical spectrum.

The term "information about an analyte" refers to information about the type of the analyte. Information about an optical spectrum characteristic to each of various substances is recorded in database previously. The information about the spectra is compared with that of a spectrum of the analyte, and the information about the analyte can be obtained from information about the similar spectra.

With respect to the spectrum, a single spectrum obtained from a single position in a measurement sample may be used, or spectra obtained from a plurality of positions in a measurement sample may be used.

3. Reagent and Reagent Kit for Preparing Measurement Sample

A reagent for use in the preparation of the measurement sample mentioned in 1 above contains a linker that is not bound to a metal nanoparticle.

A reagent kit for use in the preparation of the measurement sample mentioned in 1 above includes: a linker that is not bound to a metal nanoparticle; and metal nanoparticles that are packed separately from the linker.

EXAMPLES

The present invention is described in detail hereinafter by way of examples. However, the present invention is not intended to be limited to these examples.

1. Examples

(1) Materials

As the analytes, 20 amino acids, 39 dipeptides and 3 amyloid-β (Aβ) were used. As the linker, DSP (Dithiobis (Succinimidyl Propionate)) (Dojindo Laboratories, Product code: D629) was used. As the metal nanoparticles, gold nanoparticles φ40 nm ($9.0 \times 10^{10}$ particles/aqueous Ml solution; BBI, catalogue No. EMGC40) and the like were used.

(2) Preparation of Samples

The scheme of the sample preparation method according to examples is shown in FIG. 1.

i. An analyte solution (1 mM) (1 μL) (solvent: PBS) and a 200-04 DSP solution (14) (solvent: dimethylformamide) we reacted with each other at room temperature for 2 to 3 hours.

ii. The mixed solution (24) prepared in i, water (27 μL) and an aqueous gold nanoparticle solution (30 μL) were added dropwise to a glass bottom dish, and were then reacted with one another at room temperature for 2 to 3 hours.

iii. A 9% aqueous trifluoroacetic acid solution (1 μL) was added dropwise, and was then reacted at 4° C. overnight to form an aggregate. The aggregate was used as a SERS measurement sample.

2. Comparative Examples (Prior Art Technique)

(1) Materials

The same materials as those in Examples were used.

(2) Preparation of Samples i. A 200-μM DSP solution (1 μL) (solvent: dimethylformamide) and an aqueous gold nanoparticle solution were reacted with each other at room temperature for 2 to 3 hours.

ii. The mixed solution prepared in (i) (31 mL), an analyte solution (1 mM) (1 μL) (solvent: PBS) and water (27 μL) were added dropwise to a glass bottom dish, and were reacted with one another at room temperature for 2 to 3 hours. By this reaction, an N-terminal of the analyte was bound to each of surface-modified gold nanoparticles.

iii. A 9% aqueous trifluoroacetic acid solution (1 μL) was added dropwise, and was then reacted at 4° C. overnight to form an aggregate. The aggregate was used as a SERS measurement sample.

3. Acquisition of SERS Spectrum

For obtaining an SERS spectrum, a slit-scanning confocal Raman microscope was used. The laser irradiation was performed by a line irradiation method. The conditions for measurement were as follows.

Excitation wavelength: 660 nm

Excitation intensity: 2.5 mW/μm$^2$

Exposure time: 0.5 sec/line

Objective lens: ×40 NA1.25

4. Results

(1) Acquisition of Analyte-Specific Spectra by Examples

Figures 3A, 3B, 3C, 3D:
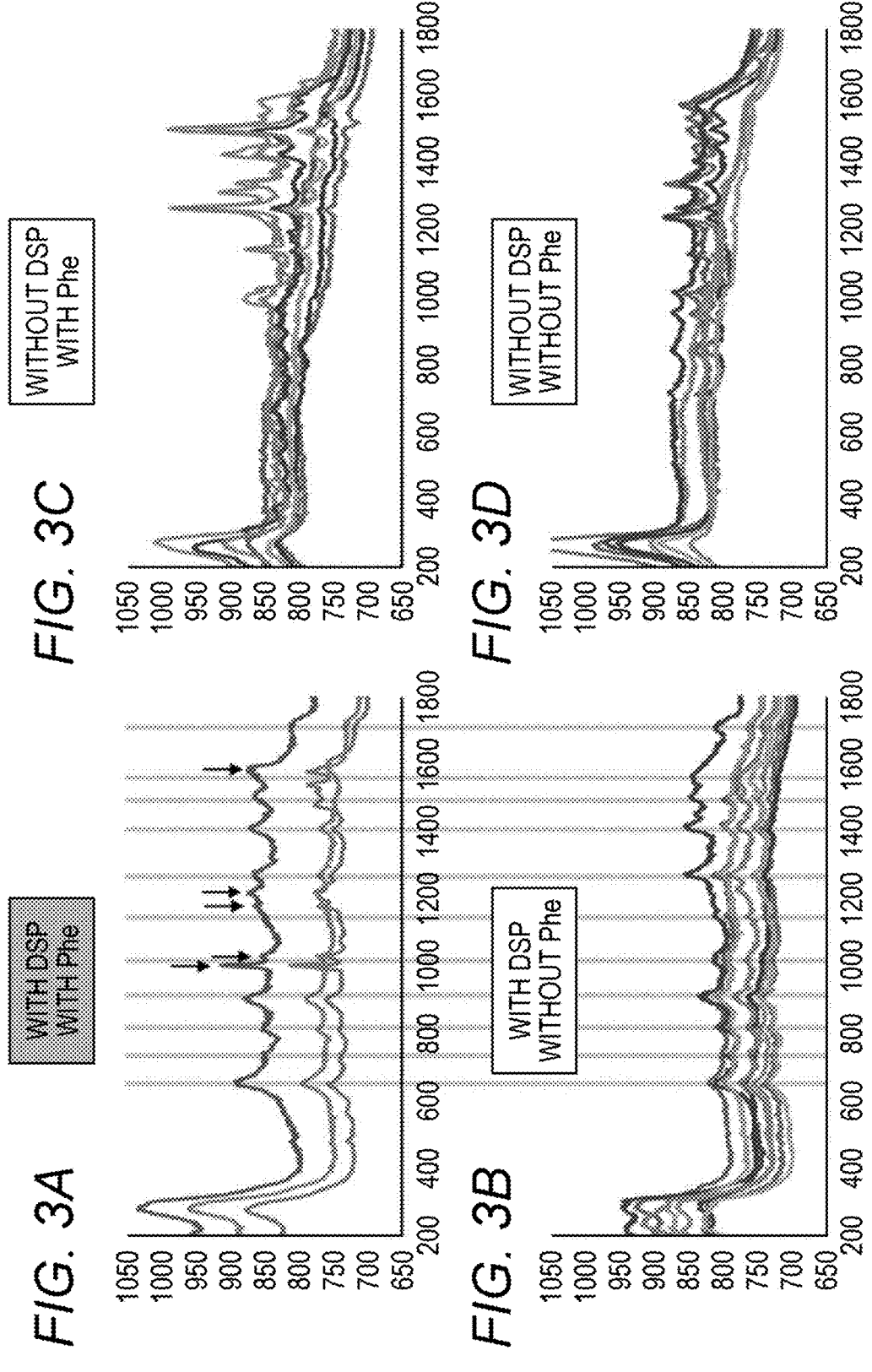
FIG. 3A shows SERS spectra of measurement samples (Phe) which are prepared in accordance with the procedure of Examples.
FIG. 3B shows SERS spectra of measurement samples which are prepared in accordance with the procedure of Examples except that no analyte is added.
FIG. 3C shows SERS spectra of measurement samples which are prepared in accordance with the procedure of Examples except that DSP is not added.
FIG. 3D shows SERS spectra of negative control samples in which neither an analyte nor DSP is added.

In order to verify as to whether or not a peak of an analyte-specific spectrum could be obtained by Examples, phenylalanine (Phe) was used as an analyte and the difference between a case where a linker was present and a case where the linker was not present was verified. Phe was added in such a manner that the final concentration of Phe in a sample became 30 μM. The results are shown in FIG. 3A to 3D. FIG. 3A shows SERS spectra of measurement samples which ware prepared in accordance with the procedure of Examples. FIG. 3B shows SERS spectra of measurement samples which ware prepared in accordance with the procedure of Examples except that no analyte was added. FIG. 3C shows SERS spectra of measurement samples which ware prepared in accordance with the procedure of Examples except that DSP was not added. FIG. 3D shows SERS spectra of negative control samples in which any analyte and DSP were not added.

Each spectrum shows an average spectrum of SERS spectrum obtained at 10 points.

As a result, in only measurement samples prepared in accordance with the procedure of Examples, peaks of analyte-dependent spectra were obtained (in FIG. 3A, points indicated by arrows were peaks).

Figure 4:
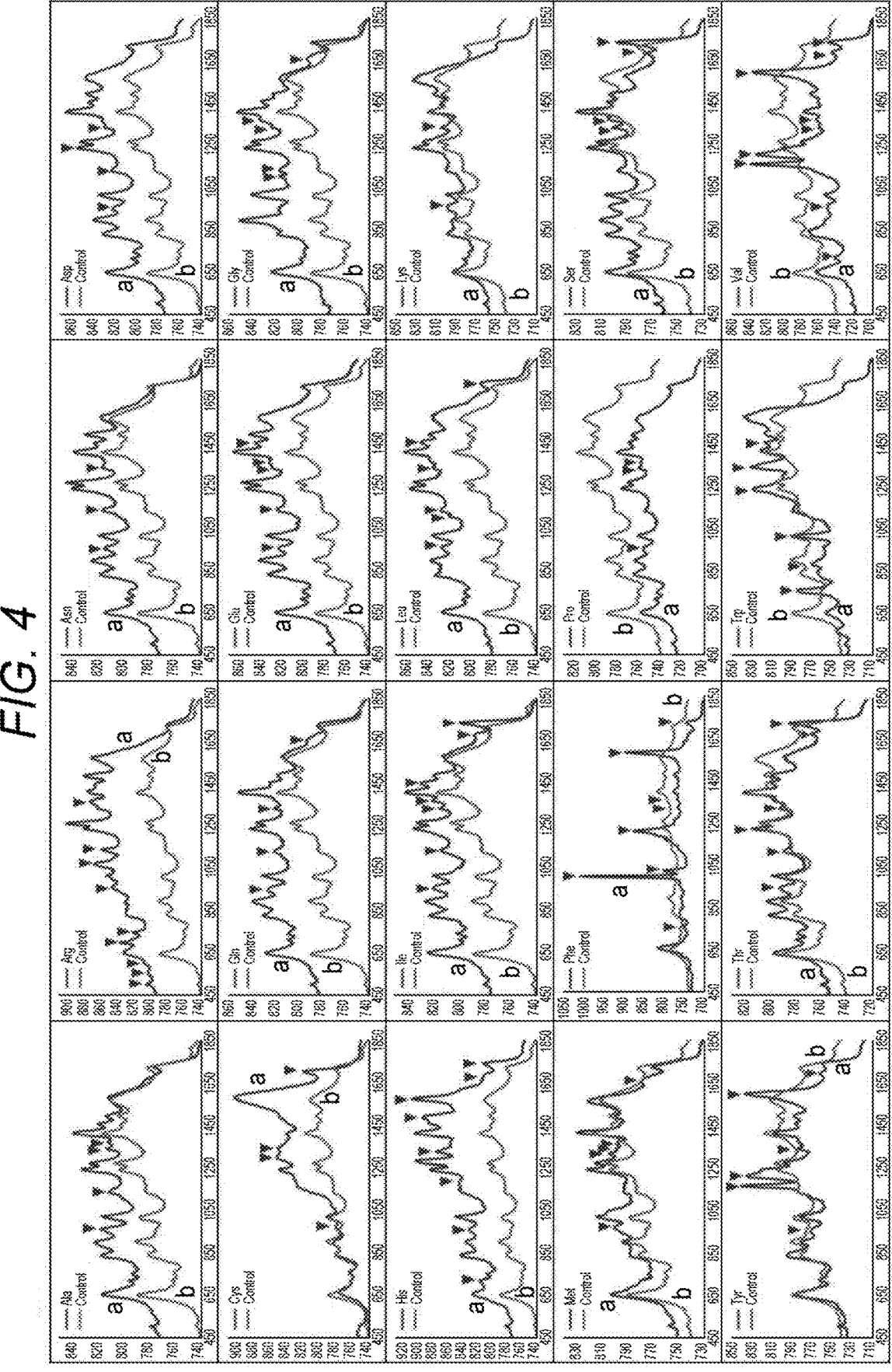
FIG. 4 shows SERS spectra obtained using 20 types of amino acids as analytes.

Next, it was verified as to whether or not a peak of an analyte-specific SERS spectrum could be obtained by using each of 20 amino acids as an analyte. The results are shown in FIG. 4. The symbol "a" in the drawings indicates an average spectrum obtained when an analyte was added, and the symbol "b" in the drawings indicates an average spectrum of a negative control which was obtained when the analyte was not added. In each of the amino acids, a peak of an analyte-dependent spectrum was obtained (in FIG. 4, positions indicated by arrow heads are peaks).

Figure 5:
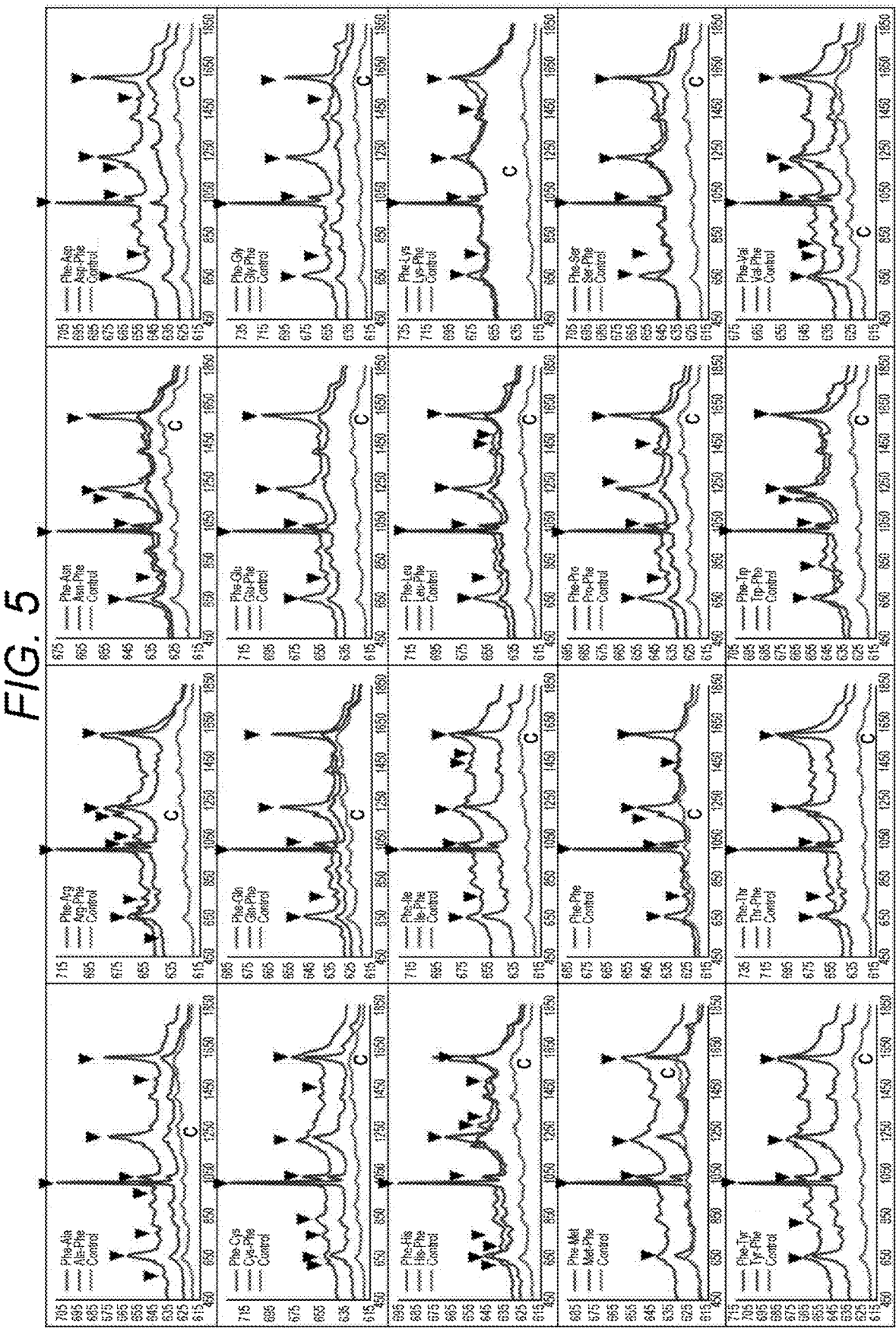
FIG. 5 shows SERS spectrum obtained using dipeptides as analytes.

Next, it was verified as to whether or not a peak of an analyte-specific spectrum could be obtained by using a dipeptide as an analyte. The dipeptides used are shown in FIG. 5. For example, with respect to a dipeptide composed of different amino acid residues (e.g., Phe-Ala, Ala-Phe), dipeptides in which the positions of the two amino acid residues were changed were prepared and an average spectrum was obtained with respect to each of the dipeptides. An average spectrum of a negative control in which no dipeptide was added was also obtained. In FIG. 5, the symbol "c" indicates a negative control. In each of the dipeptides used in the experiment, a peak of a characteristic spectrum was obtained (in FIG. 5, positions indicated by arrow heads are peaks). With respect to dipeptides composed of different amino acid residues, even when the positions of the two amino acid residues were changed, a same spectrum peak was obtained.

Figure 6A:
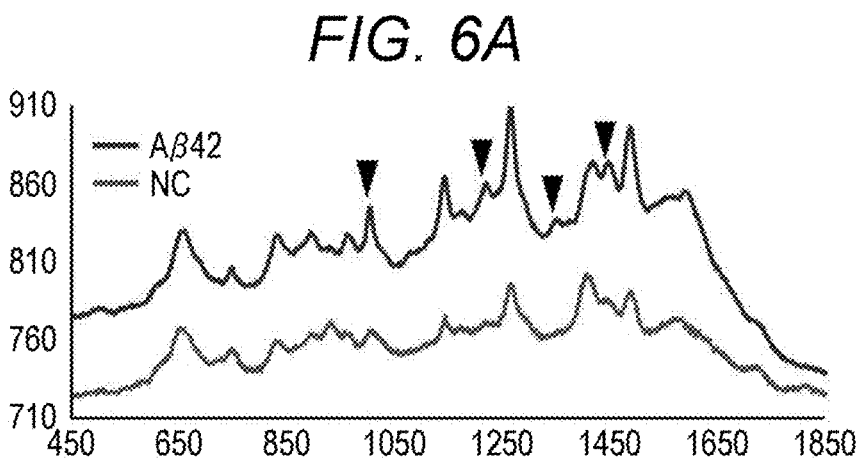
FIG. 6A shows a SERS spectrum obtained when Aβ42 is added as an analyte, and also shows a spectrum of a negative control which is obtained when the analyte is not added.
Figure 6B:
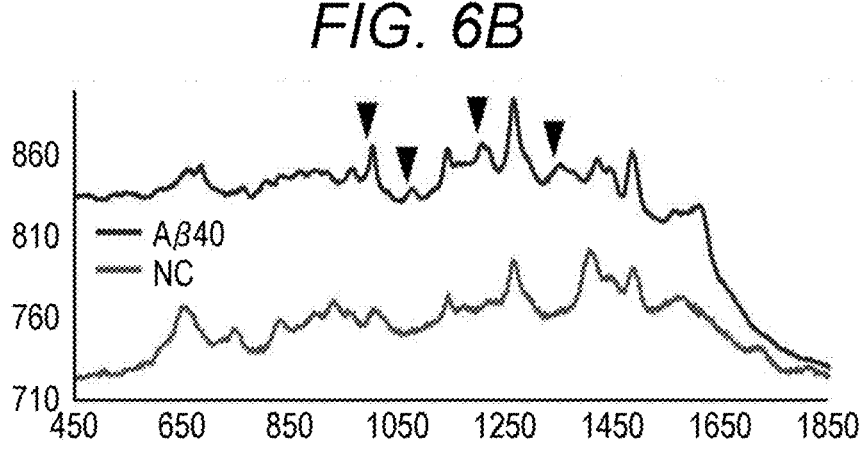
FIG. 6B shows a SERS spectrum obtained when Aβ40 is added as an analyte, and also shows a spectrum of a negative control which is obtained when the analyte is not added.
Figure 6C:
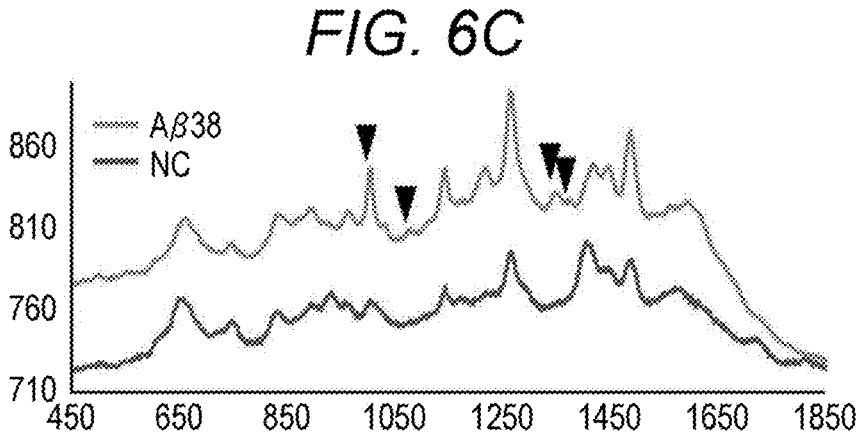
FIG. 6C shows a SERS spectrum obtained when Aβ38 is added as an analyte, and also shows a spectrum of a negative control which is obtained when the analyte is not added.
Figure 6D:
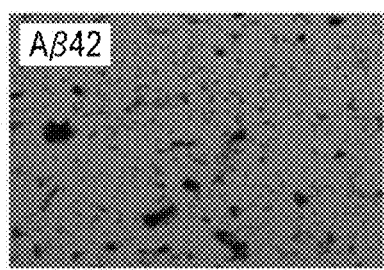
FIGS. 6D, 6E and 6F show bright-field images of aggregates of gold nanoparticles in measurement samples used for obtaining the spectra shown in FIGS. 6A, 6B and 6C, respectively.
Figure 6E:
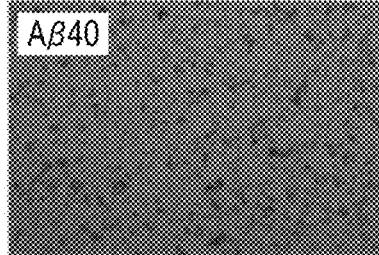
Figure 6F:
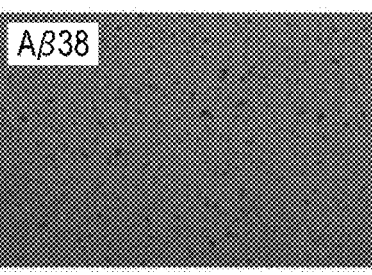
Figure 6G:
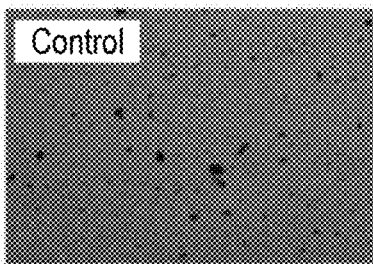
FIG. 6G shows a bright-field image of aggregates of gold nanoparticles in a measurement sample that is a negative control.

Next, it was verified as to whether or not a peak of an analyte-specific SERS spectrum could be obtained by using Aβ42, Aβ40 or Aβ38. The results are shown in FIG. 6A to 6G. FIG. 6A shows an average spectrum obtained when Aβ42 was added as an analyte, and also shows an average spectrum of a negative control which was obtained when the analyte was not added. FIG. 6B shows an average spectrum obtained when Aβ40 was added as an analyte, and also shows an average spectrum of a negative control in which the analyte was not added. FIG. 6C shows an average spectrum obtained when Aβ38 was added as an analyte, and also shows an average spectrum of a negative control in which the analyte was not added. FIGS. 6D, 6E and 6F show bright-field images of aggregates of gold nanoparticles in measurement samples used for obtaining average spectrums shown in FIGS. 6A, 6B and 6C, respectively. FIG. 6G shows a bright-field image of aggregates of gold nanoparticles in a measurement sample that was a negative control. In each of Aβ42, Aβ40 and Aβ38, a peak of a specific spectrum was obtained (in each of FIGS. 6A, 6B and 6C, positions indicated by arrow heads are peaks).

(2) Verification of Effect of Examples

The effect of Examples was verified using the measurement samples prepared by the sample preparation method employed in Examples and measurement samples prepared by the sample preparation method employed in Comparative Examples.

Figure 7:
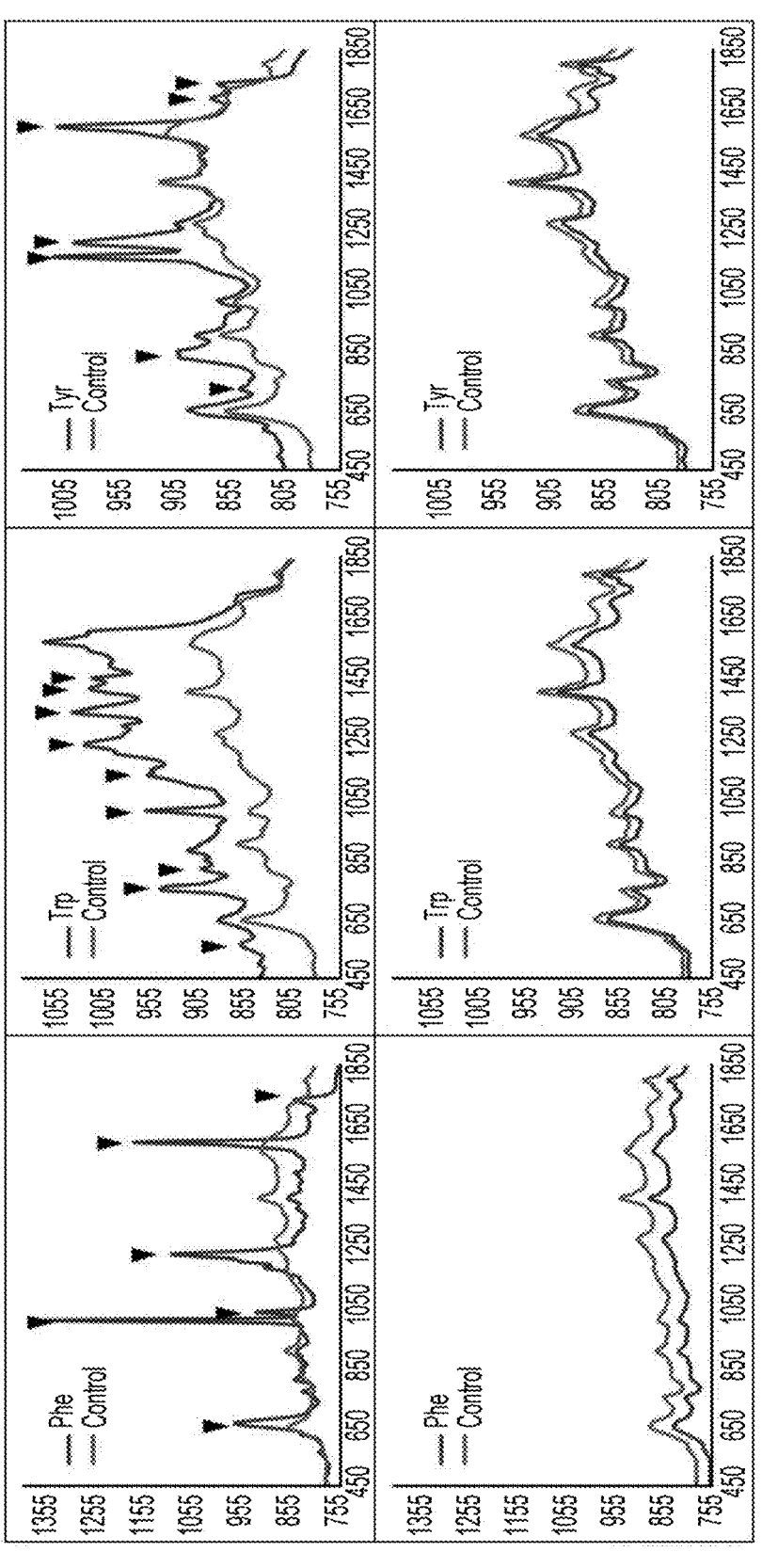
FIG. 7 shows SERS spectra of measurement samples which are prepared by the sample preparation method employed in Examples and in each of which each of phenylalanine, tryptophan and tyrosine is used as an analyte, and also shows SERS spectral of measurement samples which are prepared by the sample preparation method employed in Comparative Examples.

Average spectra were obtained using phenylalanine, tryptophan and tyrosine as analytes. With respect to negative controls, average spectra were also obtained in the same manner. The results are shown in FIG. 7. With respect to each of the measurement samples prepared by the preparation method employed in Examples, a peak of an analyte-specific peak was confirmed when any one of phenylalanine, triptophan and tyrosine was used (in FIG. 7, positions indicated by arrow heads are peaks). Meanwhile, with respect to the measurement samples prepared by the preparation method employed in Comparative Examples, a peak of an amino acid-specific spectrum was not confirmed for each of the amino acids. From these results, it was demonstrated that the detection sensitivity could be improved by the sample preparation method of Examples compared with those of Comparative Examples.

Figure 8:
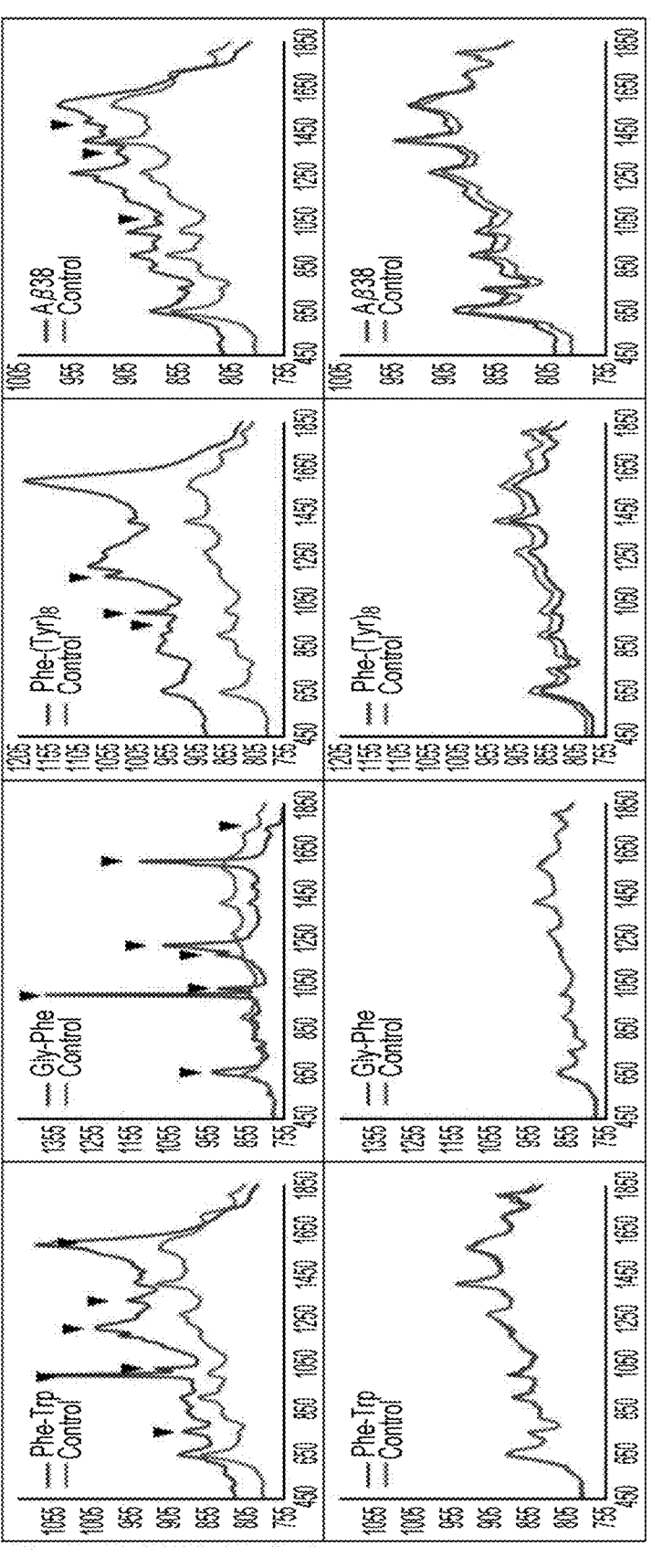
FIG. 8 shows SERS spectra of measurement samples which are prepared by the sample preparation method employed in Examples and in each of which each of dipeptides is used as an analyte, and also shows SERS spectral of measurement samples which are prepared by the sample preparation method employed in Comparative Examples.

Next, the effect of Examples was verified using the measurement samples prepared by the sample preparation method employed in Examples and measurement samples prepared by the sample preparation method employed in Comparative Examples, in which dipeptides (Phe-Trp, Gly-Phe) and Phe-(Tyr)8 and Aβ38 were used as analytes. Phe-(Tyr)8 represents a peptide in which eight tyrosine residues are linked, followed by a phenylalanine residue. With respect to negative controls, average spectra were also obtained in the same manner. The results are shown in FIG. 8. With respect to each of the measurement samples prepared by the preparation method employed in Examples, a peak of an analyte-specific spectrum was confirmed when any one of the dipeptides, Phe-(Tyr)8 and Aβ38 was used (in FIG. 8, positions indicated by arrow heads are peaks). Meanwhile, with respect to the measurement samples prepared by the preparation method employed in Comparative Examples, a peak of an amino acid-specific spectrum was not confirmed for each of the amino acids. From these results, it was demonstrated that the detection sensitivity could be improved by the measurement sample preparation method of Examples compared with those of Comparative Examples whatever the level of the molecular weight of the analyte might be (i.e., regardless of the use of a low-molecular weight substance or a high-molecular-weight substance (e.g., Aβ)).

(3) Examination of Mechanism of Enhancement of Detection Sensitivity

Figure 9:
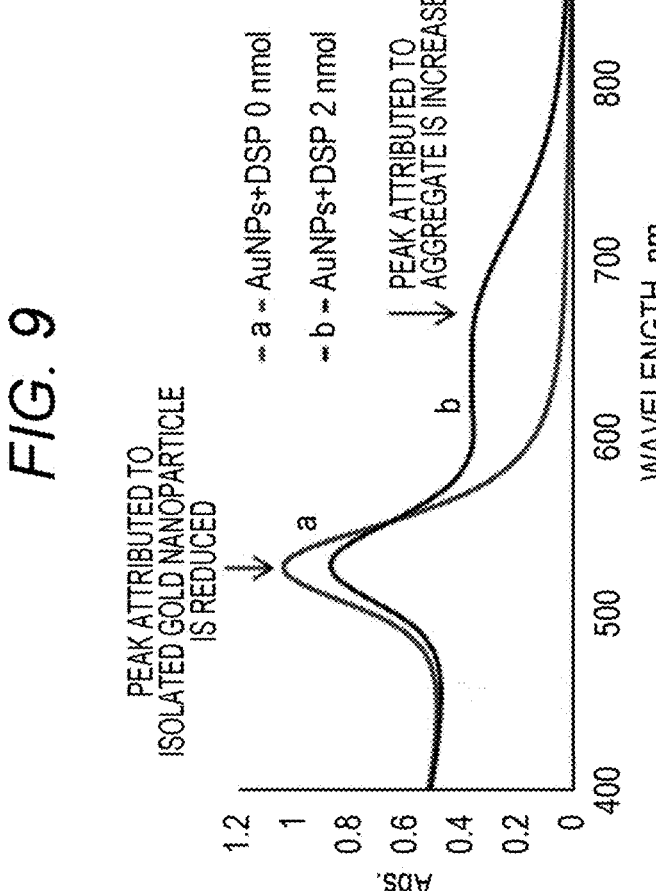
FIG. 9 shows the results obtained when a measurement sample composed of only gold nanoparticles and a measurement sample prepared by mixing only gold nanoparticles and DSP with each other are prepared and absorption spectra of the measurement samples are obtained.

Next, the reason why the detection sensitivity was enhanced in Examples was examined. A measurement sample composed of only gold nanoparticles and a measurement sample prepared by mixing only gold nanoparticles and DSP with each other were prepared, and an absorption spectrum of each of the measurement samples was obtained. The results are shown in FIG. 9. In FIG. 9, the symbol "a" indicates a spectrum of a measurement sample composed of only gold nanoparticles, and the symbol "b" indicates a spectrum of a measurement sample prepared by mixing only gold nanoparticles with DSP. The measurement sample composed of only gold nanoparticles showed one peak of an absorption spectrum at about 540 nm, while the measurement sample prepared by mixing only gold nanoparticles with DSP showed an absorption in a range from about 600 nm to about 700 nm. It was considered that this absorption was attributed to aggregates of gold nanoparticles which were formed as the result of the addition of DSP. It was considered that, in the conventional method, because the metal nanoparticles and the linker were mixed with each other in advance, the gold nanoparticles were aggregated before the binding of the analyte to the linker occurred, and therefore the analyte did not enter into the aggregates satisfactorily.

(4) Influence of Chain Length of Linker

In order to verify the influence of the chain length of a linker on detection sensitivity, measurement samples were prepared using DSP, DSH (dithiobis (succinimidyl hexanoate)) and DSU (dithiobis (succinimidyl undecanoate)), and average spectra of SERS spectra of the measurement

Figure 10:
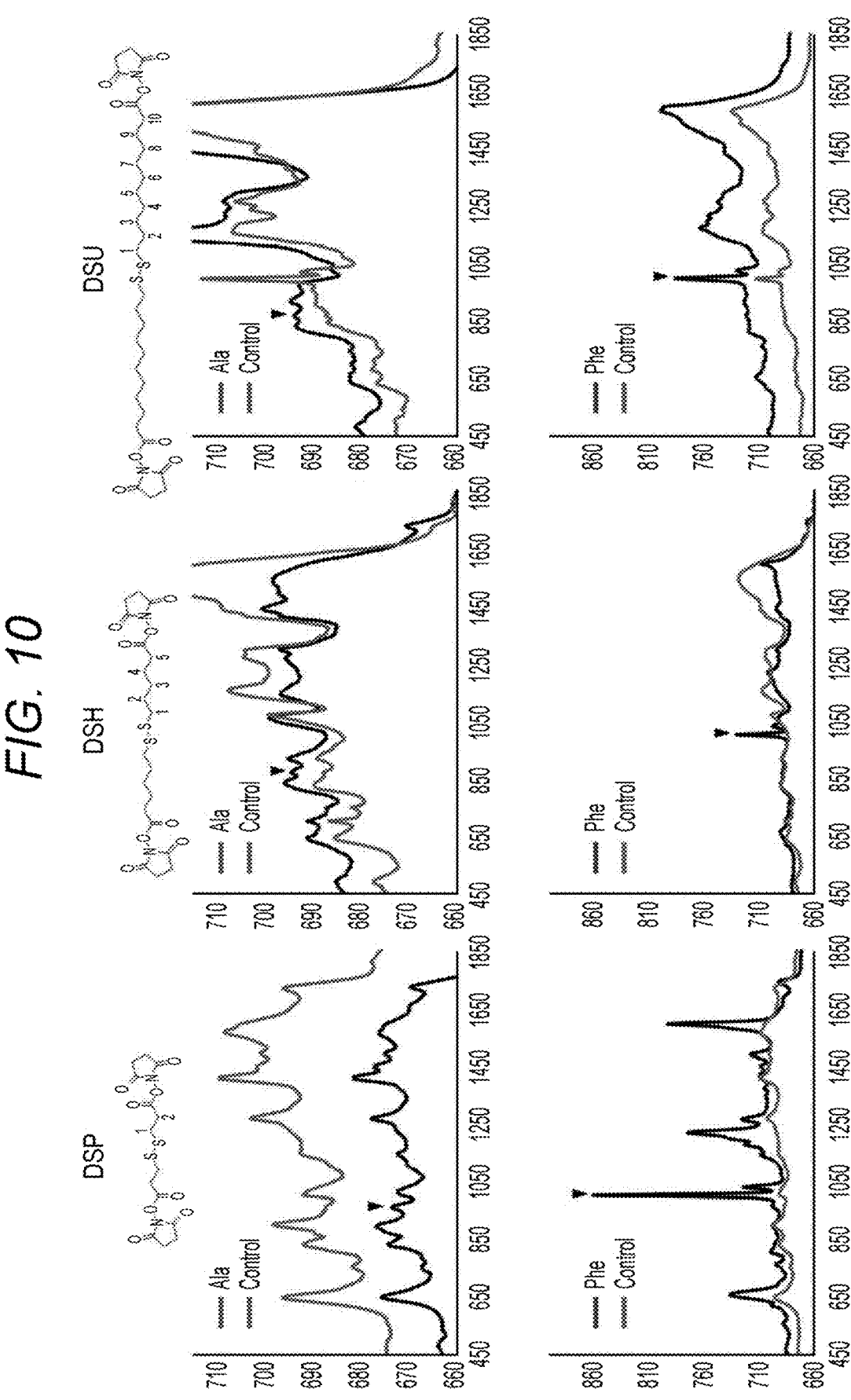
FIG. 10 shows SERS spectra which are obtained using measurement samples which are prepared using linkers having different chain lengths.

10 samples were obtained. The results are shown in FIG. 10. When each of the linkers was used, an analyte-specific spectrum peak was confirmed. From the results, it was demonstrated that the preparation method of Examples could be employed regardless of the types of the linkers.

(5) Influence of Particle Diameter and Shape of Metal Nanoparticles

Figure 11:
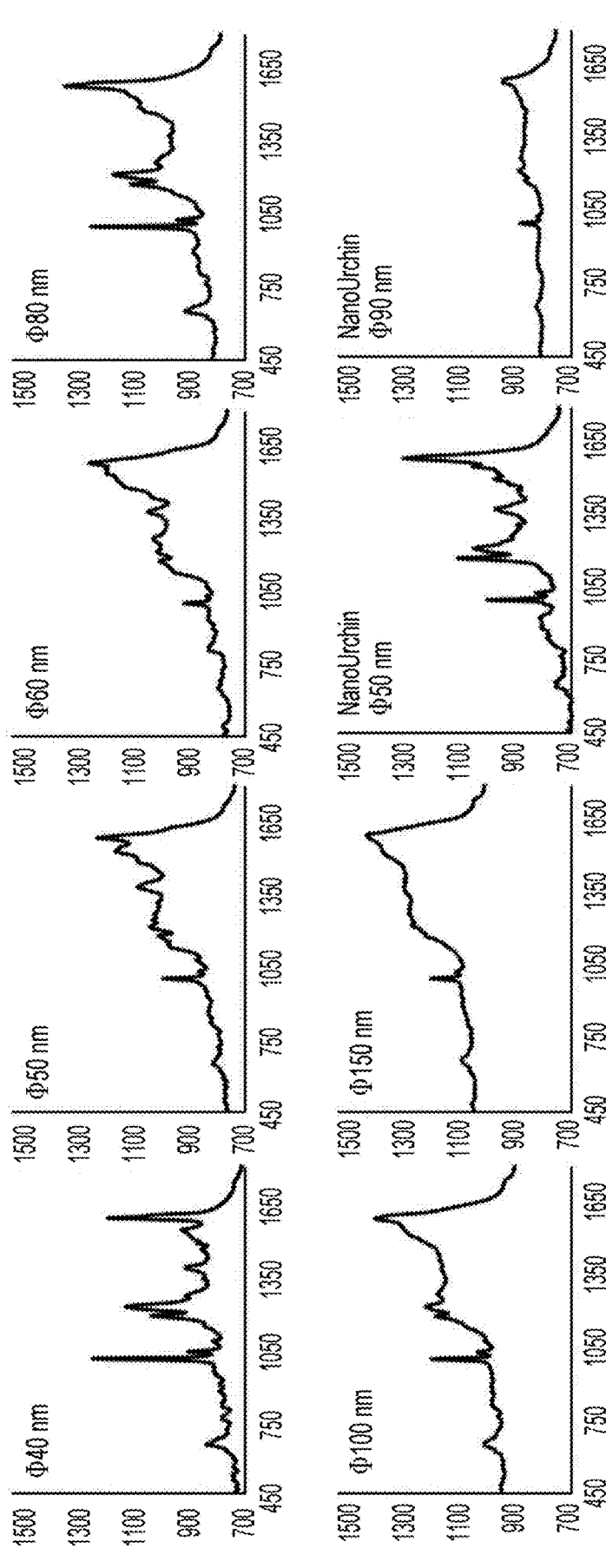
FIG. 11 shows SERS spectra which are obtained using measurement samples which are prepared using metal nanoparticles having different particle diameters and different shapes.

The influence of the particle diameter and shape of each of metal nanoparticles on detection sensitivity was examined. Using six types of spherical gold nanoparticles respectively having particle diameters of φ40 nm, φ50 nm, φ60 nm, φ80 nm, φ100 nm and φ150 nm and two types of sea-urchin-like gold nanoparticles respectively having particle diameters of φ50 nm and φ90 nm and using phenylalanine as an analyte, average spectra of SERS spectra were obtained. The results are shown in FIG. 11. With respect to each of the particle diameters and each of the shapes, a phenylalanine-specific spectrum peak was detected. Particularly with respect to spherical gold nanoparticles each having a particle diameter of φ40 nm and spherical gold nanoparticles each having a particle diameter of φ80 nm, the detection sensitivity was remarkably high.

What is claimed is:

1. An analysis method for analyzing analytes in a sample using a spectroscopic analysis, the method comprising:
preparing a measurement sample comprising, wherein the preparing comprises:
contacting the analytes with linkers to bind the analytes to the linkers, whereby a plurality of complexes are formed, each complex having the analyte and the linker bound to the analyte;
contacting the complexes with metal nanoparticles to bind the complexes to the metal nanoparticles, whereby a plurality of first aggregates are formed in a solution, each first aggregate having the metal nanoparticle and the complex bound to the metal nanoparticle; and
adding an inorganic salt or an acid to the solution containing the plurality of the first aggregates, whereby a second aggregate is formed, the second aggregate consists of a plurality of the analytes, a plurality of the linkers and a plurality of the metal nanoparticles;
obtaining an optical spectrum from the second aggregates as a measurement sample; and
outputting information about a type of the analyte in the second aggregate on the basis of the obtained optical spectrum,
wherein the analyte is at least one substance selected from the group consisting of a single amino acid, a nucleic acid, a catecholamine, a polyamine, an organic acid, an extracellular vesicle and a virus.

2. The analysis method according to claim 1, wherein the analyte has a functional group, and the linker has a reactive group capable of reacting with the functional group.

3. The analysis method according to claim 2, wherein the functional group is at least one selected from the group consisting of an amino group, a carboxyl group and a hydroxyl group.

4. The analysis method according to claim 3, wherein the functional group is an amino group and the reactive group is at least one selected from the group consisting of an N-hydroxysuccinimide ester group, an isothiocyanate group, an isocyanate group, an acyl azide group, a sulfonyl chloride group, an aldehyde group, an imide ester group, a fluorobenzene group, an epoxide group, a carbodiimide group, a carbonate group, and a fluorophenyl ester group.

5. The analysis method according to claim 4, wherein the reactive group is an N-hydroxysuccinimide ester group, and the linker is at least one component selected from the group consisting of dithiobis(succinimidyl propionate), dithiobis (succinimidyl undecanoate), dithiobis(succinimidyl octano- ate) and dithiobis(succinimidyl hexanoate).

6. The analysis method according to claim 1, wherein the metal nanoparticle is a nanoparticle, the nanoparticle being at least one metal selected from the group consisting of gold, silver, platinum, copper and palladium.

7. The analysis method according to claim 1, wherein a particle diameter of the metal nanoparticle is equal or greater than 10 nm and equal or smaller than 150 nm.

8. The analysis method according to claim 1, wherein the sample is blood, serum, plasma, saliva or a body fluid, or is a solution of the analytes in which water or a buffer solution is used as a solvent.

9. The analysis method according to claim 1, wherein the spectroscopic analysis is a surface enhanced Raman scattering analysis.

* * * * *